US008620206B2

(12) United States Patent
Brown et al.

(10) Patent No.: US 8,620,206 B2
(45) Date of Patent: *Dec. 31, 2013

(54) SYSTEM AND METHOD FOR REMOTE EDUCATION

(75) Inventors: Stephen J Brown, Woodside, CA (US); Roger J. Quy, San Mateo, CA (US)

(73) Assignee: Robert Bosch Healthcare Systems, Inc., Palo Alto, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 11/566,944

(22) Filed: Dec. 5, 2006

(65) Prior Publication Data

US 2007/0259323 A1 Nov. 8, 2007

Related U.S. Application Data

(60) Continuation of application No. 10/673,045, filed on Sep. 26, 2003, which is a continuation of application No. 09/971,785, filed on Oct. 4, 2001, now abandoned, which is a continuation-in-part of application No. 09/119,546, filed on Jul. 20, 1998, now Pat. No. 6,330,426, which is a continuation-in-part of application No. 08/953,883, filed on Oct. 20, 1997, now abandoned, which is a continuation-in-part of application No. 08/757,129, filed on Dec. 3, 1996, now Pat. No. 6,144,837, which is a continuation of application No. 08/334,643, filed on Nov. 4, 1994, now Pat. No. 5,601,435, said application No. 09/119,546 is a continuation of application No. 08/958,786, filed on Oct. 29, 1997, now Pat. No. 5,913,310, which is a continuation-in-part of application No. 08/857,187, filed on May 15, 1997, now Pat. No. 5,918,603, which is a division of application No. 08/247,716, filed on May 23, 1994, now Pat. No. 5,678,571.

(51) Int. Cl.
*G09B 3/00* (2006.01)

(52) U.S. Cl.
USPC .......................................... 434/350; 434/236

(58) Field of Classification Search
USPC .................... 434/236, 262, 350, 322
See application file for complete search history.

(56) References Cited

U.S. PATENT DOCUMENTS 3,808,502 A 4/1974 Babilius
4,110,918 A 9/1978 James et al.
(Continued)

FOREIGN PATENT DOCUMENTS

WO WO-93/02622 2/1993
WO WO-94/16774 8/1994

OTHER PUBLICATIONS

Howe, Kenneth; Diary of an AOL Addict / One Man's Confessions of His Online Obsession; San Francisco Chronicle; Apr. 5, 1995, p. D1.*

(Continued)

*Primary Examiner* — Kang Hu
(74) *Attorney, Agent, or Firm* — Maginot, Moore & Beck

(57) ABSTRACT

The invention describes a system and method for allowing an individual to view an educational program remotely. In the preferred embodiment, the invention is used as a healthcare education system. The system comprises a file server which is connected to a database holding the educational programs. A remote interface connected to the file server allows an administrator to assign educational programs to an individual. The remote interface also includes a memory card writer which records the individual's identification code and the address of the file server on a memory card. The individual is given the memory card to take home. When the individual places the memory card in the memory card reader of a multimedia processor, the processor uses the file server address to automatically connect to the file server. The file server receives the individual's identification code from the processor, retrieves the corresponding educational program from the database, and sends the program to the processor to be displayed. After the individual has watched the educational program, completion data in the form of the date and time the program was watched, or the individual's response, is sent from the multimedia processor to the file server. The completion data can then be viewed by the administrator on a report screen.

41 Claims, 7 Drawing Sheets

(56) References Cited

U.S. PATENT DOCUMENTS

| | | | |
|---|---|---|---|
| 4,130,881 A | | 12/1978 | Haessler et al. |
| 4,347,851 A | | 9/1982 | Jundanian |
| 4,360,345 A | | 11/1982 | Hon |
| 4,539,435 A | * | 9/1985 | Eckmann .................... 379/76 |
| 4,576,578 A | | 3/1986 | Parker et al. |
| 4,700,055 A | * | 10/1987 | Kashkashian, Jr. .......... 235/379 |
| 4,729,381 A | | 3/1988 | Harada et al. |
| 4,749,354 A | | 6/1988 | Kerman |
| 4,779,199 A | | 10/1988 | Yoneda et al. |
| 4,796,639 A | | 1/1989 | Snow et al. |
| 4,803,625 A | | 2/1989 | Fu et al. |
| 4,858,617 A | | 8/1989 | Sanders |
| 4,907,973 A | | 3/1990 | Hon |
| 4,933,873 A | | 6/1990 | Kaufman et al. |
| 4,952,928 A | * | 8/1990 | Carroll et al. .............. 340/10.41 |
| 5,019,974 A | | 5/1991 | Beckers |
| 5,024,225 A | | 6/1991 | Fang |
| 5,025,374 A | | 6/1991 | Roizen et al. |
| 5,056,059 A | | 10/1991 | Tivig et al. |
| 5,120,230 A | | 6/1992 | Clark et al. |
| 5,222,020 A | | 6/1993 | Takeda |
| 5,226,431 A | | 7/1993 | Bible et al. |
| 5,277,197 A | | 1/1994 | Church et al. |
| 5,307,263 A | | 4/1994 | Brown |
| 5,377,258 A | * | 12/1994 | Bro .......................... 379/106.02 |
| 5,377,353 A | * | 12/1994 | Yamaguchi .................. 711/147 |
| 5,454,722 A | | 10/1995 | Holland et al. |
| 5,497,772 A | * | 3/1996 | Schulman et al. ............ 600/347 |
| 5,507,288 A | | 4/1996 | Bocker et al. |
| 5,596,994 A | * | 1/1997 | Bro ............................ 600/545 |
| 5,597,307 A | | 1/1997 | Redford et al. |
| 5,601,435 A | | 2/1997 | Quy |
| 5,624,265 A | | 4/1997 | Redford et al. |
| 5,678,571 A | | 10/1997 | Brown |
| 5,722,418 A | * | 3/1998 | Bro ............................ 600/545 |
| 5,791,342 A | * | 8/1998 | Woodard ..................... 600/300 |
| 5,792,047 A | * | 8/1998 | Coggins ...................... 600/300 |
| 5,982,889 A | * | 11/1999 | DeMont ...................... 705/51 |
| 5,995,976 A | * | 11/1999 | Walker et al. ............. 707/104.1 |
| 6,009,469 A | * | 12/1999 | Mattaway et al. ............ 709/227 |
| 6,011,991 A | * | 1/2000 | Mardirossian ............... 600/544 |
| 6,039,688 A | * | 3/2000 | Douglas et al. .............. 600/300 |
| 6,076,068 A | * | 6/2000 | DeLapa et al. ................ 705/14 |
| 6,108,665 A | * | 8/2000 | Bair et al. ................. 707/104.1 |
| 6,119,164 A | * | 9/2000 | Basche ........................ 709/229 |
| 6,144,837 A | | 11/2000 | Quy |
| 6,249,809 B1 | * | 6/2001 | Bro ............................ 709/217 |
| 6,334,778 B1 | | 1/2002 | Brown |
| 2003/0126593 A1 | | 7/2003 | Mault et al. |
| 2004/0106855 A1 | | 6/2004 | Brown et al. |

OTHER PUBLICATIONS

Introducing the Next Generation of About Your Diabetes, U.S. Pharmacopical Convention and American Diabetes Association, (1993).

Shandle, Jack, "Who Will Dominate The Desktop in the 90's?", , Electronics, Feb. 1990, pp. 48-50. (3 pages) Cited by 2 patents.

Alere Medical Inc 's First Supplemental Response to Plaintiffs's Amended Interrogatory No. 2. Jun. 20, 2008.

U.S. Appl. No. 90/010,053—Order Granting Request for Ex Parte Reexamination, Jan. 18, 2008.

U.S. Appl. No. 90/009,237_Request_for_Re-examination_5601435_Aug. 1, 2008.

* cited by examiner

FIG. 3

PROGRAM ASSIGNMENT SCREEN

AVAILABLE PROGRAMS:          STUDENTS:

- [X] DIABETES AND EXERCISE     [X] DAN LINDSEY
- [ ] FOOD EXCHANGES AND DIET   [ ] MARK SMITH
- [ ] BLOOD GLUCOSE MONITORING  [ ] DEAN JONES

[ADD NEW PROGRAM] [SAVE NEW LISTING] [ADD NEW PATIENT]

[ASSIGN PROGRAM] [DELETE PROGRAM]

FIG. 4

REPORT SCREEN

| STUDENT | ASSIGNED PROGRAM | PROGRAM COMPLETED | RESULTS/SCORE |
|---|---|---|---|
| DAN LINDSEY | DIABETES AND EXERCISE | MAY 1, 1997, 5:22 PM | COMPLETED |
| MARK SMITH | FOOD EXCHANGES AND DIET | MAY 3, 1997 3:54 PM | 79 |
| DEAN JONES | BLOOD GLUCOSE MONITORING | NOT COMPLETED | N/A |

Thank you for watching "Living With Diabetes", brought to you by Acme Pharmaceuticals. Please answer the following questions by pushing the numbered button on your remote control which corresponds to the best answer.

A. Do you visit your doctor regularly?
    1 - yes    2 - sometimes    3 - no

B. Do you monitor your sugar (glucose) intake?
    1 - yes    2 - sometimes    3 - no C. Do you exercise regularly?
    1 - yes    2 - sometimes    3 - no

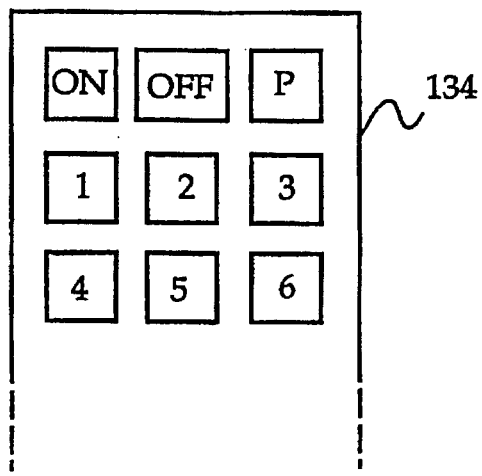

*FIG. 5*

SYSTEM AND METHOD FOR REMOTE EDUCATION

PRIORITY CLAIM

This application is a Continuation of application Ser. No. 10/673,045, filed Sep. 26, 2003, which is a Continuation of application Ser. No. 09/971,785, filed Oct. 4, 2001, which is a Continuation-In-Part of application Ser. No. 09/119,546 filed Jul. 20, 1998, now U.S. Pat. No. 6,330,426, issued Dec. 11, 2001, which is a Continuation-In-Part of application Ser. No. 08/953,883 filed Oct. 20, 1997, now abandoned, which is a Continuation-In-Part of 08/757,129 filed Dec. 3, 1996, now U.S. Pat. No. 6,144,837 issued Nov. 7, 2000, which is a Continuation of U.S. application Ser. No. 08/334,643 filed on Nov. 4, 1994, now U.S. Pat. No. 5,601,435 issued Feb. 11, 1997.

Application Ser. No. 09/119,546 filed Jul. 20, 1998, is also a Continuation of application Ser. No. 08/958,786, filed Oct. 29, 1997, now U.S. Pat. No. 5,913,310, issued Jun. 22, 1999, which is a Continuation-In-Part of application Ser. No. 08/857,187, filed May 15, 1997, now U.S. Pat. No. 5,918,603, issued Jul. 6, 1999, which is a Divisional of application Ser. No. 08/247,716, filed May 23, 1994, now U.S. Pat. No. 5,678,571, issued Oct. 21, 1997.

All of the above applications are herein incorporated by reference.

FIELD OF THE INVENTION

The present invention generally relates to remote education systems. More particularly, this present invention relates to a system and method of remote health education in which an individual is provided with a memory card capable of being placed in a multimedia processor to automatically access selected educational health programs.

BACKGROUND OF THE INVENTION

One of the biggest problems many healthcare providers face is their patients' lack of knowledge. Patients may lack knowledge on basic preventative measures, such as why they should exercise, eat right, and not smoke. Patients may also lack knowledge on conditions or diseases they do have, such as how to measure their blood glucose levels if they are diabetic. This lack of knowledge is a problem for healthcare providers because patients who do not know how to take care of themselves are ill more frequently. Thus, they must visit their doctors more often, sometimes incurring additional costs for hospital stays or laboratory tests. This results in greater fees for the patient, his or her insurance company, and often the taxpayers.

An example of this problem is seen in some diabetes patients. Diabetic patients must regularly receive insulin shots and adhere to a specific diet in order to control their blood glucose levels. Unfortunately, some diabetic patients do not understand all the reasons why they should have regular insulin shots or why they should or should not eat certain foods. In addition, many diabetic patients are unaware of the health consequences should they not follow their treatment plan. As a result, such patients are sicker and require more healthcare than those patients who understand all aspects of their diseases. Sicker patients require more healthcare, which is expensive and time-consuming for healthcare professionals, insurance companies, and the patients themselves.

One way this problem is handled is by increasing the amount of education patients receive about their lifestyle choices and/or their diseases. When patients know what they need to do to stay healthy, they are less inclined to visit their doctors as frequently. In addition, if patients understand the health problems that will result from not taking care of themselves, they will be more likely to follow their prescribed treatments.

Educational forms range from pamphlets in a doctor's office to radio announcements to television shows. Paper-based educational material is cheap, easy to produce, and easy to distribute. Unfortunately, pamphlets or articles are limited to words and pictures and are usually quite boring, which makes it unlikely that patients will enjoy and remember reading them. Radio announcements and television shows are more lively and entertaining, but they are broadcast to the general public. Thus they cannot be customized to a particular patient.

Due to technological advances, patients can now be educated using CD-ROMs, the Internet, and multimedia processors. U.S. Pat. No. 5,307,263 by the present inventor discloses a modular, microprocessor-based health monitoring system. The hand-held unit has a display screen, a control button pad, interchangeable program cartridges, and sensors for monitoring a variety of healthcare data. The program cartridges include motivational and educational material related to use of the device, including step-by-step instructions. Acquired data may be transmitted to a data management unit via an interface cable, or to a clearing house via telephone lines. A program cartridge for monitoring glucose levels and a glucose sensor is disclosed for the purpose of caring for children with diabetes.

U.S. Pat. Nos. 5,597,307 and 5,624,265 by Redford and Stem describe an educational system and apparatus aimed at children which also uses a multimedia processor. This invention comprises a remote control located in a book or other printed publication. A child can read the book while watching the display generated by the multimedia processor, and then press the buttons in the remote control book to alter what he sees.

None of the above education systems allow an individual to automatically access assigned educational programs remotely. The inventions described above provide general educational programs which are not tailored to any one individual. Neither system provides confirmation that an individual has completed the educational program. Neither system allows a healthcare provider nor teacher to easily custom-design which educational programs a patient or individual is to view. Finally, neither system provides a patient or individual access to an unlimited number of educational programs.

OBJECTS AND ADVANTAGES OF THE INVENTION

In view of the above, it is an object of the present invention to provide an individual with a remote education system which can be accessed from the individual's home. It is another object of the invention to provide a remote education system which displays educational programs for an individual. It is another object of the present invention to provide interactive educational programs. Another object of the invention is to provide a remote education system comprising a memory card containing an individual's identification code and the locations of educational programs for the individual to View. It is another object of the present invention to provide confirmation that an individual has completed an educational program. It is another object of the invention to provide a remote education system through the Internet. Yet another object of the present invention is to provide a remote healthcare education system for patients. It is another object of the present invention to allow a healthcare provider to assign educational programs for a patient by using a memory card.

These and other objects and advantages will become more apparent after consideration of the ensuing description and the accompanying drawings.

SUMMARY OF THE INVENTION

The present invention comprises a system and method for remote education using a memory card. The system preferably comprises a database, a file server, a remote interface, a memory card writer, a display unit, a multimedia processor, and a card reader. The file server acts as a central hub of the system, because it is preferably coupled to the database, the remote interface, and the multimedia processor. Accordingly, these three components are capable of being located at long distance from one another. The database preferably stores a plurality of educational programs. Preferably, the remote interface allows an administrator, such as a healthcare provider or educator, to assign an educational program to an individual. The identification code of the individual and a pointer referring to the assigned educational program are preferably stored on memory means of the file server. Preferably, by using the memory card writer, the administrator is capable of recording the individual's identification code and the address of the file server onto the memory card.

After the administrator assigns the particular educational program to the individual, the memory card can be given to the individual. When the individual wishes to view the assigned educational program, the individual simply places the card in the card reader. Preferably, the memory card reader is coupled to or located with the multimedia processor, which in turn is coupled to the file server. Upon receiving the memory card, the multimedia processor preferably sends the individual's identification code to the file server. Preferably, the file server then calls up the assigned educational program from the database. The content of the educational program is sent to the multimedia processor and displayed on a display unit for the individual.

Preferably, the file server is notified when the individual has completed the educational program. Completion data includes the date and time the individual watched the educational program. Further, the completion data can also include responses made by the individual to the educational program. Preferably, the file server records the completion data and then send the completion data to the remote interface for the administrator to review.

In the preferred embodiment of the remote education system, the file server is a web server, the remote interface is an interactive web page, and the communication link is the Internet. An administrator assigns an educational program to the individual by entering the assignment information onto the web page. The assignment information is sent to the web server where it is held. When the individual places the memory card into the card reader, the multimedia processor sends the individual's identification code to the web server, which calls up the educational program from the database. In the preferred embodiment, the database can comprise one or more web servers, which allows the administrator to assign to the individual an unlimited amount of material.

In the preferred embodiment, the memory card is a plastic card with a magnetic information strip, similar to an ordinary credit card. The magnetic strip contains the individual's identification code and the location of the file server. In another embodiment, the memory card comprises a circuit. The circuit contains the individual's identification code and the location of the file server.

BRIEF DESCRIPTION OF THE DRAWINGS

The preferred and alternative embodiments of the present invention are described in detail below with reference to the following drawings.

FIG. 3 is a sample program assignment screen as displayed on the remote interface;

FIG. 4 is a sample report screen as displayed on the remote interface;

FIG. 5 is a sample interactive educational program as displayed by the multimedia processor;

DETAILED DESCRIPTION OF THE PREFERRED EMBODIMENT

The present invention provides a system and method for remotely educating an individual using a memory card. In the preferred embodiment, the invention is used to distribute custom-designed health education programs to patients. However, it is to be understood that the invention is not limited to the healthcare industry. The system and method of the invention may be used for any type of remote education application in any field.

Figure 1:
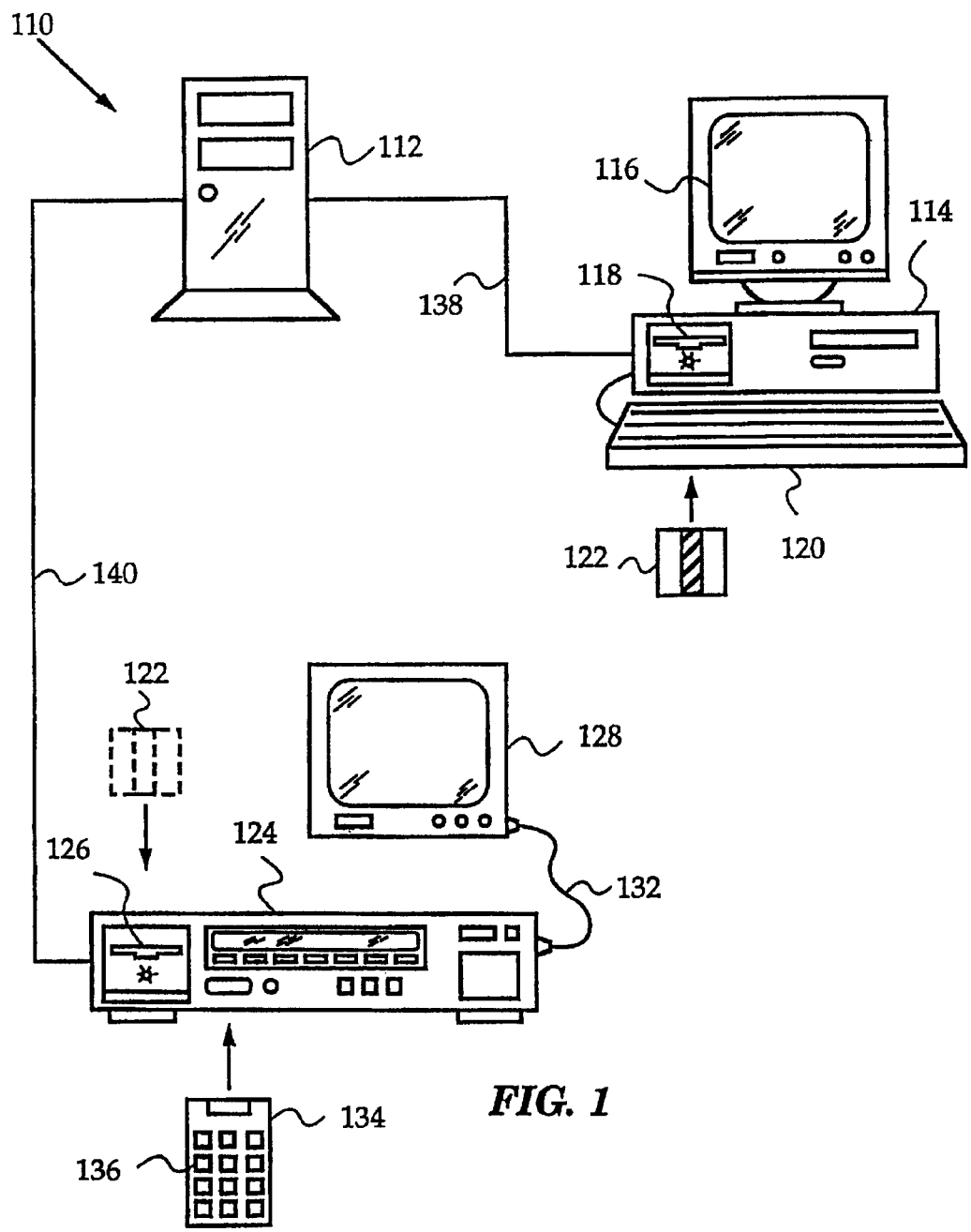
FIG. 1 is a schematic diagram of a remote education system according to a preferred embodiment of the present invention.

The preferred embodiment of the system is shown in FIG. 1. The system 110 comprises a file server 112, which is connected by communication links 138, 130, and 140 to a remote interface 114, a database 148 containing educational programs, and a multimedia processor 124. File server 112 is preferably a world wide web server, remote interface 114 is preferably a web page, and communication links 138 and 130 are preferably the Internet. Remote interface 114 has a display 116 and a keyboard 120, which an administrator can use to assign an educational program to an individual.

Remote interface 114 also contains or is connected to a memory card writer 118. Memory card writer 118 is used to record the individual's identification code and the location of file server 118 on a memory card 118. Preferably, the location of file server 118 is in the form of a uniform resource locator, or URL.

Communication link 140 from file server 112 to multimedia processor 124 is preferably the Internet. However, file server 112 and multimedia processor 124 can also contact each other via wireless communication networks, cellular networks, telephone networks, or any other suitable network. Multimedia processor 124 is also connected by communication link 132 to a display 128, which is used to show educational programs to the individual. Communication link 132 can be any suitable connection means. Display 128 is a standard audiovisual display, such as a television.

Multimedia processor 124 contains or is connected to a memory card reader 126. When memory card 118 is placed in memory card reader 126, the assignment information is sent to file server 112, which retrieves the assigned educational program from database 148. The educational program content is then sent through communication link 40 to multimedia processor 124 and shown on display 128. In addition, microprocessor 124 can also comprise expansion ports to support additional user interfaces and devices, such, as keyboards and trackballs, as well as add-on circuits for enhanced sound, video, or processing performance (not shown).

As shown in FIG. 3, input device 134 comprising numerous momentary contact push buttons 136 is used by the individual to control and respond to the educational program. Push buttons 136 represent control functions, such as "on" and "off", as well as numbers, letters, or various commands, such as "yes" and "no". Alternatively, push buttons 136 may be replaced by switches, keys, a touch sensitive display screen, or any other data input device. Input device 134 is a standard wireless communication means which sends command signals to multimedia processor 124 to be processed and executed. However, any communication means which allows input device 134 to connect with multimedia processor 124.

For clarity of illustration, only one database and only one multimedia processor are shown in FIG. 1. It is to be understood that system 110 may include any number of databases for storing any number of educational programs, and any number of multimedia processors for use by any number of individuals.

Figure 2:
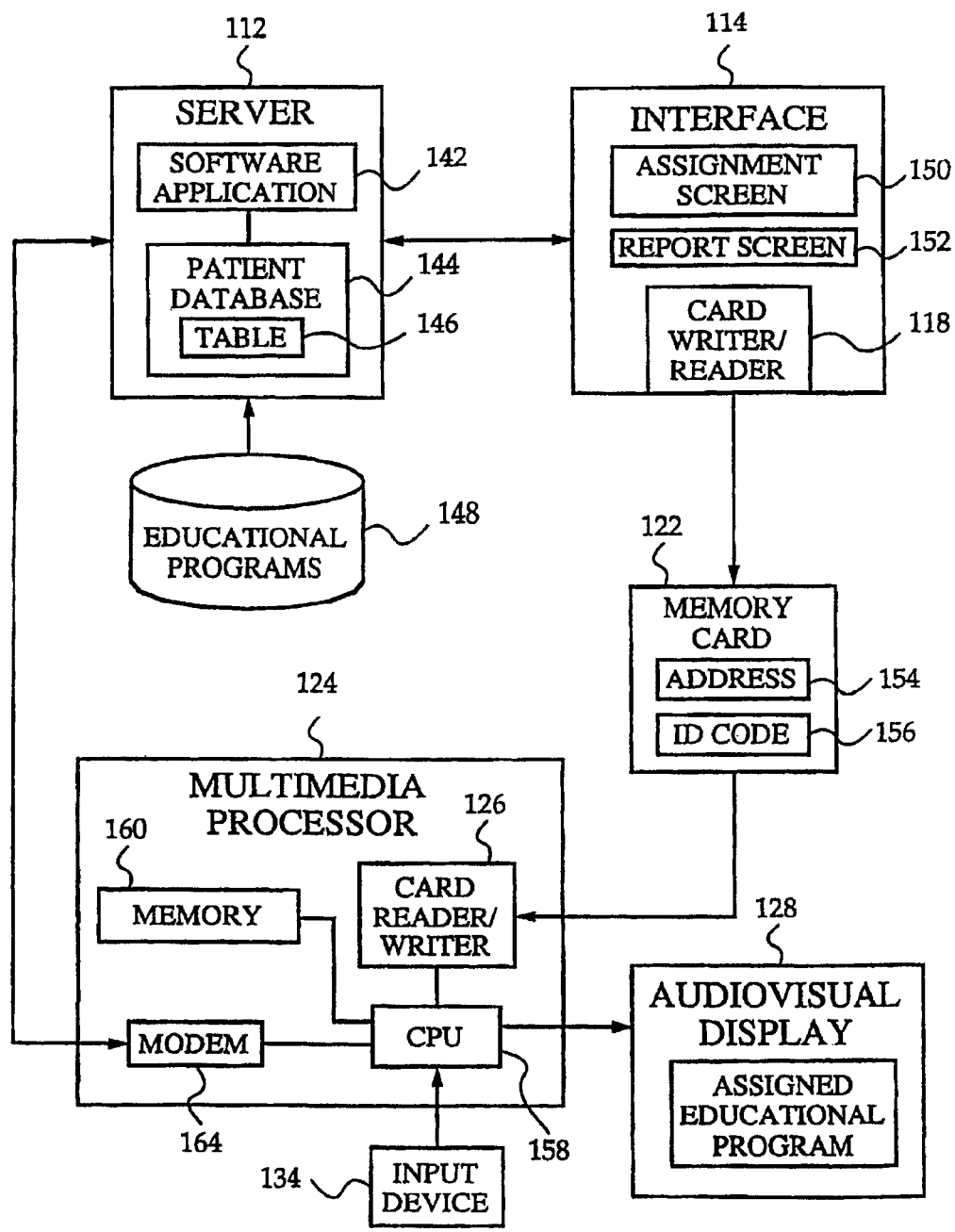
FIG. 2 is a block diagram showing the components of the remote education system and how they are connected, according to FIG. 1.

FIG. 2 shows a detailed block diagram of the preferred embodiment of the invention illustrated in FIG. 1. Server 112 includes a general software application 142 which is used create a database 144 and a patient table 146. Software application 142 is also capable of programming file server 112 to carry out standard commands such as receiving, saving, and transmitting information. Database 144 contains the educational programs 148. Alternatively, database 144 can contain pointers to educational programs 148 which are located in remote databases. The advantage of the pointers is that they allow the healthcare provider to assign any number of educational programs 148, as long as educational programs 148 can be transmitted to multimedia processor 124 and shown on display 28. Thus suitable forms of educational programs 148 include photos, videos, animation, static web pages, interactive web pages, etc. Patient table 146, which is stored in the memory of file server 112, lists the patients, their identification codes, and educational programs 148 which have been assigned to them.

Patient table 146 is generated by information entered into the assignment screen 150 of remote interface 114. Assignment screen 150, which is illustrated in FIG. 3, lists available educational programs 148, each with a corresponding check box 166, and patients, also each with a corresponding check box 168. The administrator brings up assignment screen 150 on display 116 of remote interface 114. She selects a check box 168 for a patient and then selects a check box 166 corresponding to educational program 148 to be assigned to the patient. More than one educational program 148 can be assigned to each patient. In addition, more than one patient can be assigned the same educational program 148. The administrator then selects the ASSIGN PROGRAM button 70, which stores the assignment in patient table 146. Assignment screen 150 also includes a DELETE PROGRAM button 72, which allows the administrator to erase the assignment.

New listings of patients and educational programs 148 can easily be created by the administrator by clicking on the ADD NEW PATIENT button 174 or the ADD NEW PROGRAM button 176. When these buttons are selected, a new field is added to the patient or program categories. The administrator then types in the name of the new patient or the name of the new educational program 148, and saves the addition by clicking on the SAVE NEW LISTING button 178. The new listings are then saved in patient table 146.

In the preferred embodiment, remote interface 114 is a web page. Thus, using keyboard 120, as shown in FIG. 1, the administrator can create customized educational programs 148 in the form of static or interactive web pages for patients. The administrator creates the web page using a scripting language such as HTML or Java, and then stores it on database 144. These web pages can be accessed by multimedia processor 124 in the same manner as the above mentioned educational programs 148.

Referring to FIG. 2 again, remote interface 114 also comprises a report screen 152 which is shown on display 116. Report screen 152, as illustrated in FIG. 4, tells the administrator when the patient has completed watching assigned educational program 148 and/or a program score. Specific techniques for writing report generator program to display data in this manner are well known in the art.

The program score is generally determined by evaluating the patient's responses to an interactive educational program, such as an interactive web page. FIG. 5 shows a sample educational program 148 which includes questions for the patient to answer using input device 134.

The remote education system also includes a memory card writer 18 connected to remote interface 114. Memory card writer is an apparatus which can encode information onto a magnetic strip or circuit. The process of storing information on a magnetic strip or circuit is well known. Memory card 122 produced contains the patient's identification code 156 and the file server address 154.

As shown in FIG. 2, multimedia processor 124 also comprises a memory means 160, a central computing unit (CPU) 158, a modem 164, and audiovisual display 128. Memory card reader 126, memory means 160, modem 164, and audiovisual display 128 are all connected to CPU 158. Multimedia processor 124 connects to file server 112 using modem 164 and communication link 40, which is preferably a telephone cable. Multimedia processor 124 can be programmed to automatically dial out using modem 164 whenever memory card 122 is placed in memory card reader 126.

Memory card reader 126 comprises means of detecting and interpreting the information stored on memory card 122. In the preferred embodiment, memory card reader 126 is a magnetic strip reader. When the patient places memory card 122 in memory card reader 122, the information is sent to CPU 150 and then memory means 160. The information is then sent to file server 112 by way of modem 164.

Memory means 160 of multimedia processor 124 is also for storing program instructions on how to connect to file server 112 and how to transmit patient's identification code 156. In addition, memory means 160 receives and stores assigned educational programs 148 from file server 112. When the content of educational programs 148 are sent to multimedia processor 124 from file server 112, memory means translate the content into audiovisual signals to be displayed on display 128.

Figure 6A:
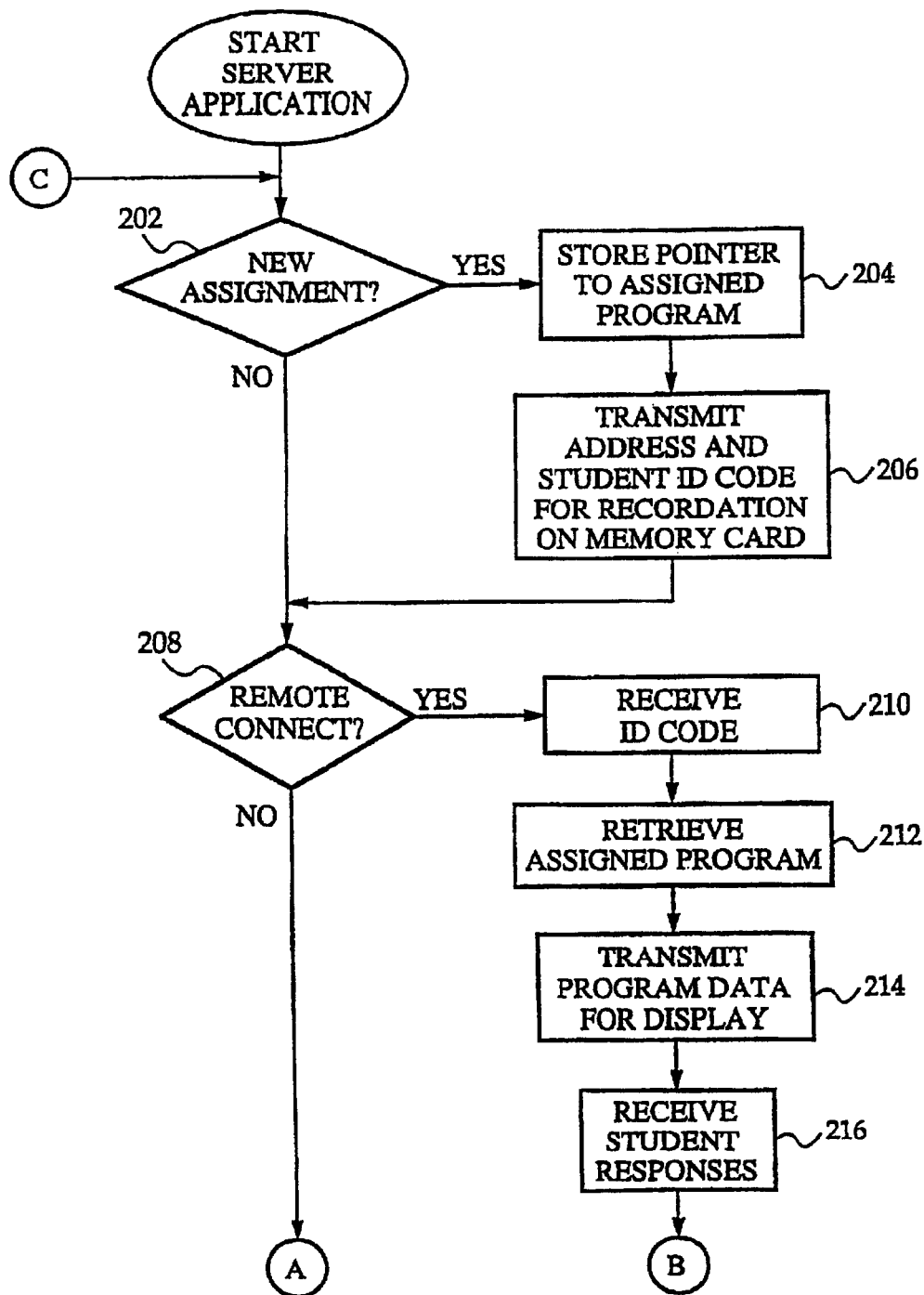
FIG. 6A is a flow chart illustrating the steps executed by the file server of the present invention as shown in FIG. 1.
Figure 6B:
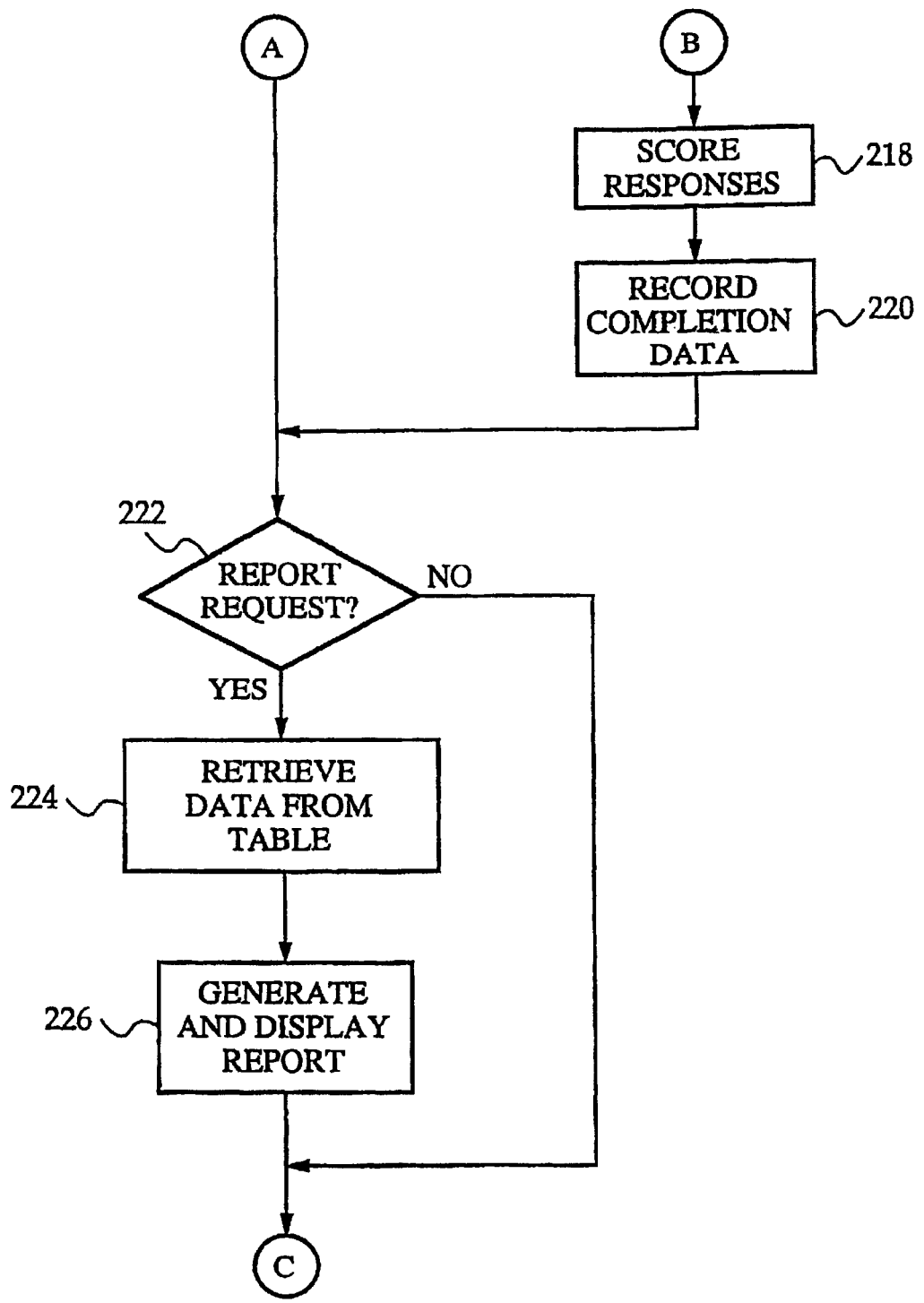
FIG. 6B is a continuation of the flow chart of FIG. 6A.

FIGS. 6A and 6B show a flowchart illustrating the steps carried out by server 112 in the preferred embodiment of the invention. In step 202, server 112 first asks if the administrator would like to create a new assignment. Creating a new assignment can mean adding a new patient to the patient list or assigning a new educational program 148 to a patient. If the administrator decides to create a new assignment, the information is stored in patent table 146, as shown in step 204. In step 206, the new assignment information consisting of the patient's identification code 156 and file server address 154 is also recorded on memory card 122 by memory card writer 118, and then given to the patient. If the administrator does not need to create a new assignment, she goes directly from step 202 to step 208.

After the patient returns home, he places memory card 122 in memory card reader 126 connected to multimedia processor 124. File server address 154 on memory card 122 allows multimedia processor 124 to locate and connect to file server 112 in step 208. Patient's identification code 156 is then sent over in step 210. In step 212, file server 112 then goes to patient table 146 and looks up educational program 148 assigned to patient. A pointer in database 144 then retrieves educational program 148. If educational program 148 is located in a remote database, it is sent through file server 112 to multimedia processor 124, as shown in step 214. Memory means 160 of multimedia processor 124 then interpret and translate the content of educational program 148 into audiovisual signals to be shown on display 128.

After the patient has watched educational program 148, completion data comprising the time and date or patient responses is sent from multimedia processor 124 to file server 112 in step 216. Step 218 scores the patient responses to determine a program score. Step 220 then records the completion data in patient table 146 of file server 112.

If the administrator wishes to view completion data of a particular patient, she can request a patient report, as shown in step 222. Step 222 can occur after the patient has watched and responded to educational program 148 in step 220, or at any time after step 208. File server 122 retrieves the patient's completion data from patient table 146, step 224, and then shows it in the form of report screen 152 on display 116 in step 226. Report screen 152 is illustrated in FIG. 4.

Figure 7:
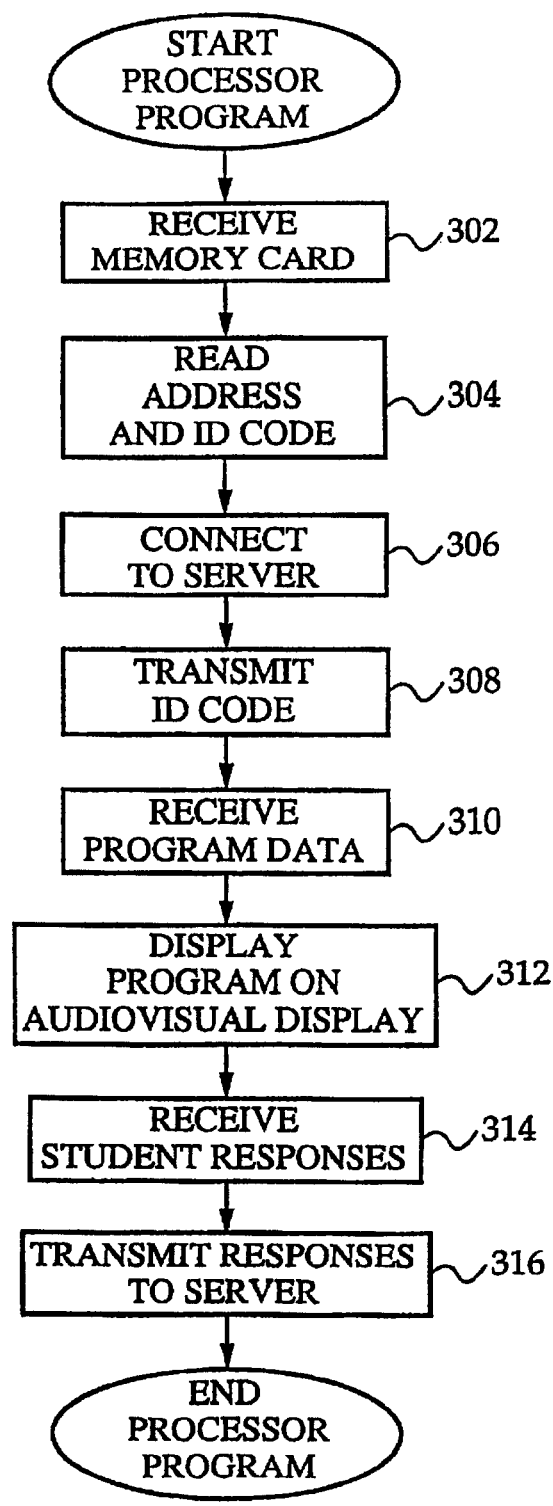
FIG. 7 is a flow chart illustrating the steps executed by the multimedia processor of the present invention as shown in FIG. 1.

FIG. 7 is a flowchart outlining the steps involved in the processor program of multimedia processor 124 in the preferred embodiment of the invention. Processor program can be carried out by known software programs. The processor program begins when memory card 122 is placed in memory card reader 126, as shown in step 302. Memory card reader 126 reads patient's identification code 304 and file server address 156 from memory card 122 in step 304, and then sends the information to CPU 158. File server address 156 allows CPU 158 to connect to server 112 via modem 164 in step 306. Patient's identification code 154 is then transmitted to file server 112 in step 308. In step 310, CPU 158 receives the content of assigned educational program 148 via modem 164. The content is converted into audiovisual signals shown on display 128 in step 312. Patient response to educational program 148 is sent to CPU 158 by input device 134. CPU 158 then sends the patient response, along with other completion data, to file server 112. The processor program of multimedia processor 124 then ends.

Memory card reader 126 of multimedia processor 124 can also have a writing function similar to that of memory card writer 118 of remote interface 114. This feature allows the patient responses to educational program to be stored on memory card 122. The patient can then bring in memory card 122 to his healthcare provider or the administrator. Memory card writer 118 of remote interface 114 must also have reading capabilities. Memory card 122 is inserted in memory card writer/reader 118 and the patient responses are downloaded into remote interface 114. This feature can be used if the patient does not wish to transmit his responses over communication link 140.

The present invention allows a healthcare provider or administrator to assign a remote educational program to a patient. The patient has the luxury of watching and responding to the program in his own home at his convenience. The patient's response to the educational program is then transmitted to the file server and displayed for the administrator to view. Thus the administrator can monitor whether or not the patient has watched the educational program, and can also evaluate his responses to the program.

Appendix A shows one implementation of the present invention as it applies to working with a diabetes patient through MEDTV™ over the Internet. MEDTV™ is a trademark of Raya Systems, Inc. (Mountain View, Calif.).

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible, as this invention can be used in any field where it is desirable to remotely educate an individual. For example, teachers can use it to assign lessons to their students, and employers can use it to provide additional job training for their employees.

Another embodiment of the present invention allows companies to promote their products. Preprogrammed memory cards can be placed with a company's products. When the consumer buys a product, he also receives the preprogrammed memory card, which contains the product identification code and the address of the company's consumer-product file server. When the consumer places the memory card in the memory card reader of his multimedia processor, the multimedia processor automatically connects to the company's file server. The file server contains a consumer-product table which stores a list of all the company's products with corresponding pointers to relevant educational programs or advertisements. For example, a sunblock product would have a pointer to a short video on basic sun safety, as well as an advertisement for all sunblock products made by that company.

When the file server receives the product identification code from the multimedia processor, it retrieves the relevant educational program or advertisement and sends it back to the consumer's multimedia processor. The consumer can then watch the program or advertisement on the display.

Considering all the possibilities of the remote education system, the scope of the invention should be determined not by the examples given, but by the appended claims and their legal equivalents.

The invention claimed is:

1. A system to distribute media programs, comprising:
a processor unit configured to present material to an individual and receive responses from the individual; and
one or more servers configured to communicate with the processor unit through at least one communication network and access a non-transitory computer readable medium on the processor unit for storing one or more media programs, wherein (i) the one or more servers are remotely situated from the processor unit, (ii) the processor unit establishes communication with a particular server of the one or more servers based on an identification code input by said individual and a destination address programmed on the medium by a physician prior to said individual receiving said processor unit, (iii) the one or more servers are configured to communicate one of the one or more media programs to the processor unit based upon the identification code, (iv) the processor unit is configured to communicate the responses received from the individual to the particular server, (v) the identification code is (a) stored on the medium of the processor unit and (b) used to direct the media program to a particular individual or a group of individuals and (vi) the destination address is (a) stored on the medium of the processor unit and (b) comprises data readable by the processor unit to cause said processor unit to establish communication with said particular server.

2. The system according to claim 1, wherein the one or more media programs comprise at least one educational program.

3. The system according to claim 1, wherein the one or more media programs comprise at least one advertisement related program.

4. The system according to claim 1, wherein the individual plugs a data storage card into a card reader coupled to the processor unit.

5. The system according to claim 1, wherein the one or more media programs comprise at least one health related program.

6. The system according to claim 5, wherein the at least one health related program comprises education material concerning one or more health related topics selected from the group consisting of preventative measures, exercise, diet, lifestyle, health conditions, diseases, health consequences, health monitoring and self-care.

7. The system according to claim 4, further comprising an interface unit remotely situated from the server and the processor unit, wherein the interface unit is configured to communicate with the server and the processor unit.

8. The system according to claim 7, wherein the interface unit and the processor unit are configured to write information and read information to and from the data storage card.

9. The system according to claim 8, wherein the data storage card comprises a plastic card with a magnetic strip.

10. The system according to claim 8, wherein the data storage card comprises a memory circuit.

11. The system according to claim 7, wherein the media program communicated to the processor unit is assigned to the individual by a healthcare provider using the interface unit.

12. The system according to claim 11, wherein the media program is assigned based upon a condition or disease being managed by the individual.

13. The system according to claim 7, wherein the individual is a student and the media program communicated to the processor unit is assigned to the student by a teacher using the interface unit.

14. The system according to claim 7, wherein the individual is an employee and the media program communicated to the processor unit is assigned to the employee by an employer using the interface unit.

15. The system according to claim 14, wherein the media program comprises job training information.

16. The system according to claim 1, wherein each of the one or more media programs is tailored to a particular individual.

17. The system according to claim 1, wherein the processor unit is configured to communicate with the server via a wireless network.

18. The system according to claim 1, further comprising an input device configured to communicate one or more responses from the individual to the processor unit.

19. The system according to claim 1, wherein the at least one communication network comprises a network type or a combination of two or more network types selected from the group consisting of wireless networks, cellular networks, telephone networks, satellite networks, broadcast networks, digital broadcast networks, digital television networks and cable networks.

20. The system according to claim 1, wherein the one or more media programs comprise one or more elements selected from the group consisting of photos, videos, animation, static web pages and interactive web pages.

21. A method for distributing media programs, comprising the steps of:
(A) storing one or more media programs in a non-transitory computer readable medium accessible by one or more servers, wherein said one or more servers are configured to communicate with one or more remotely located processor units via at least one communication network;
(B) associating one or more pointers to said one or more media programs stored in said non-transitory computer readable medium with one or more identification codes received from an individual, wherein said one or more identification codes are used to direct said one or more media programs to said individual or a group of individuals; and
(C) programming said processor units with a destination address programmed by a physical prior to said individual receiving one of said processor units, wherein (i) said one or more identification codes and said destination address establish a communication link with a particular server of the one or more servers, (ii) said processor units each store said one or more identification codes and said destination address on said medium, and (iii) said destination address comprises data readable by the one or more processor units to cause the one or more processor units to establish communication with the particular server.

22. The method according to claim 21, wherein the one or more media programs comprise at least one educational program.

23. The method according to claim 21, wherein the one or more media programs comprise at least one advertisement related program.

24. The method according to claim 21, wherein the individual plugs one or more data storage cards into a card reader coupled to each of the one or more processor units.

25. The method according to claim 21, wherein the one or more media programs comprise at least one health related program.

26. The method according to claim 25, wherein the at least one health related program comprises education material concerning one or more health related topics selected from the group consisting of preventative measures, exercise, diet, lifestyle, health conditions, diseases, health consequences, health monitoring and self-care.

27. The method according to claim 24, wherein each of said one or more data storage cards is packaged with a product.

28. The method according to claim 27, wherein the step of distributing said one or more data storage cards to one or more individuals comprises selling said product.

29. The method according to claim 27, wherein at least one of said one or more media programs comprises advertisement or educational material related to the product.

30. The method according to claim 27, wherein each of said one or more identification codes comprises a product identification code.

31. The method according to claim 21, wherein each of the one or more media programs comprise one or more elements selected from the group consisting of photos, videos, animation, static web pages and interactive web pages.

32. The method according to claim 24, wherein at least one of said one or more data storage cards comprises a plastic card with a magnetic strip.

33. The method according to claim 24, wherein at least one of said one or more data storage cards comprises a memory circuit.

34. The method according to claim 24, wherein said one or more remotely located processor units are configured to (i) read said one or more data storage cards and (ii) automatically establish a communication link with said server using said destination address.

35. A non-transitory computer readable medium containing computer readable data including:
- an identification code received by an individual, wherein said identification code is (i) stored on said non-transitory computer readable medium and (ii) used to direct one or more media programs to a particular individual or group of individuals; and
- destination address information for establishing a communication link between a particular server of one or more servers and a processor unit, wherein (a) the one or more servers are remotely situated from the processor unit, (b) the one or more servers are configured to communicate at least one of one or more media programs stored in a computer accessible database to the processor unit via at least one communication network based upon the identification code and said destination address information, (c) the processor unit is configured to access the non-transitory computer readable medium and (d) the processor unit is configured to (i) read from the non-transitory computer readable medium the identification code and destination address information to cause the processor unit to establish the communication link with the particular server, (ii) present the at least one of the one or more media programs received from the server to an individual and (iii) communicate one or more responses received from the individual to the server via the at least one communication network.

36. The non-transitory computer readable medium according to claim 35, wherein the one or more media programs comprise at least one educational program.

37. The non-transitory computer readable medium according to claim 35, wherein the one or more media programs comprise at least one advertisement related program.

38. The non-transitory computer readable medium according to claim 35, wherein the individual plugs the non-transitory computer readable medium into a card reader coupled to the processor unit.

39. The non-transitory computer readable medium according to claim 35, wherein the one or more media programs comprise at least one health related program.

40. The non-transitory computer readable medium according to claim 39, wherein the at least one health related program comprises education material concerning one or more health related topics selected from the group consisting of preventative measures, exercise, diet, lifestyle, health conditions, diseases, health consequences, health monitoring and self-care.

41. The non-transitory computer readable medium according to claim 35, further containing computer readable data encoding the one or more responses received from the individual, wherein the processor unit is further configured to write the one or more responses received from the individual to the non-transitory computer readable medium.

* * * * *